US008999161B2

(12) United States Patent
Mathias et al.

(10) Patent No.: US 8,999,161 B2
(45) Date of Patent: Apr. 7, 2015

(54) PLASMA FILTER WITH LAMINATED PREFILTER

(75) Inventors: Jean Marie Mathias, Gesves (BE); Yves Poubeau, Le Magny (FR)

(73) Assignee: Fenwal, Inc., Lake Zurich, IL (US)

( * ) Notice: Subject to any disclaimer, the term of this patent is extended or adjusted under 35 U.S.C. 154(b) by 392 days.

(21) Appl. No.: 13/399,503

(22) Filed: Feb. 17, 2012

(65) Prior Publication Data

US 2012/0228207 A1      Sep. 13, 2012

Related U.S. Application Data

(60) Provisional application No. 61/451,716, filed on Mar. 11, 2011.

(51) Int. Cl.

| B01D 29/56 | (2006.01) |
| B01D 61/14 | (2006.01) |
| A61M 1/02 | (2006.01) |
| B01D 39/16 | (2006.01) |
| B01D 39/20 | (2006.01) |
| A61M 1/36 | (2006.01) |

(52) U.S. Cl.
CPC ........... *A61M 1/0272* (2013.01); *A61M 1/0281* (2013.01); *B01D 39/1623* (2013.01); *B01D 39/2017* (2013.01); *B01D 2239/0654* (2013.01); *A61M 1/3636* (2014.02)

(58) Field of Classification Search
CPC .... B01D 69/12; B01D 39/1623; B01D 69/10; B01D 2239/065; B01D 39/2017; B01D 2239/0654; B01D 35/30; A61M 1/0272; A61M 1/0281; A61M 1/3636

USPC ................ 210/295, 335, 483, 488, 489, 490, 210/500.21, 500.26, 503, 505, 506, 507, 210/508
See application file for complete search history.

(56) References Cited

U.S. PATENT DOCUMENTS

| 5,885,457 A | 3/1999 | Breillatt |
| 6,669,905 B1 | 12/2003 | Mathias et al. |
| 2001/0037078 A1 | 11/2001 | Lynn |
| 2004/0118770 A1* | 6/2004 | Sale et al. ..................... 210/488 |
| 2005/0186553 A1 | 8/2005 | Herman |

FOREIGN PATENT DOCUMENTS

EP            1 506 808 A1      2/2005

OTHER PUBLICATIONS

Extended European Search Report for EP Appln 12155919.9 dated May 21, 2012.

* cited by examiner

*Primary Examiner* — John Kim
(74) *Attorney, Agent, or Firm* — Cook Alex Ltd.

(57) ABSTRACT

A plasma filter is provided for separating aggregates and targeted blood cell species from plasma comprising a filter housing with an inlet and an outlet and an internal flow path between the inlet and outlet. A filter media is disposed in the flowpath between the inlet and the outlet for filtering plasma that passes therethrough. The filter media comprises a filter configured to substantially remove targeted blood cell types from the plasma and a prefilter upstream of the filter, the prefilter having at least one reinforcement layer.

20 Claims, 4 Drawing Sheets

US 8,999,161 B2

PLASMA FILTER WITH LAMINATED PREFILTER

CROSS REFERENCE TO RELATED APPLICATION

This application claims the benefit of the filing date of U.S. Provisional Application Ser. No. 61/451,716 filed Mar. 11, 2011, the entire contents of which is incorporated by reference herein.

FIELD OF THE DISCLOSURE

This disclosure relates generally to the processing of whole blood and, more particularly, to a filter assembly for use in such processing.

BACKGROUND

Most whole blood collected today is separated into its clinically useful components for storage, further processing and/or administration. This includes plasma, which is required by regulation to contain no more than specified maximum levels of residual red blood cells, leukocytes and platelets. As a result, the systems for collecting and/or processing plasma commonly include filtration devices to remove cellular blood species.

SUMMARY OF THE DISCLOSURE

The present subject matter has a number of aspects which may be used in various combinations, and the disclosure of one or more specific embodiments is for purposes of disclosure and description and not limitation. This summary only highlights a few of the aspects of this subject matter and additional aspects are disclosed in the drawings and more detailed description that follows.

In connection with one aspect of the present disclosure, a plasma filter is provided for separating aggregates and targeted blood cell species from plasma comprising a filter housing with an inlet and an outlet and an internal flow path between the inlet and outlet. A filter media is disposed in the flowpath between the inlet and the outlet for filtering plasma that passes therethrough. The filter media comprises a filter configured to substantially remove targeted blood cell types from the plasma and a prefilter upstream of the filter, the prefilter having at least one reinforcement layer.

In another aspect of the disclosure, a plasma filter is provided comprising a first housing layer, a prefilter for removing aggregates from the plasma; first and second filter membranes having pore sizes to remove targeted cellular blood species from plasma by exclusion; a mesh layer; and a second housing layer, wherein the prefilter is laminated to at least one reinforcement layer. Preferably, the reinforcement layer for the prefilter comprises a non-woven polyester fabric. The prefilter maybe laminated either to a single reinforcement layer or between two reinforcement layers.

In a further aspect of the disclosure, the reinforced prefilter may be sealed only to the first housing layer at a seal which is interior of the seal of the first and second housing layers with the first and second filter membranes. Additionally, the mesh layer may be sealed only to the second housing layer at a seal which is interior of the seal of the first and second housing layers with the first and second filter membranes.

DETAILED DESCRIPTION

A more detailed description of a plasma filter in accordance with the present disclosure is set forth below. It should be understood that the description below of specific devices is intended to be exemplary, and not exhaustive of all possible variations. Thus, the scope of the disclosure is not intended to be limiting, and should be understood to encompass variations or embodiments that would occur to persons of ordinary skill.

Examples of manual blood processing and storage systems are described generally in U.S. Pat. No. 6,669,905, which is incorporated herein by reference. The systems described therein include a membrane filter for removing the residual red blood cells, platelets, and leukocytes from plasma.

Figure 1:
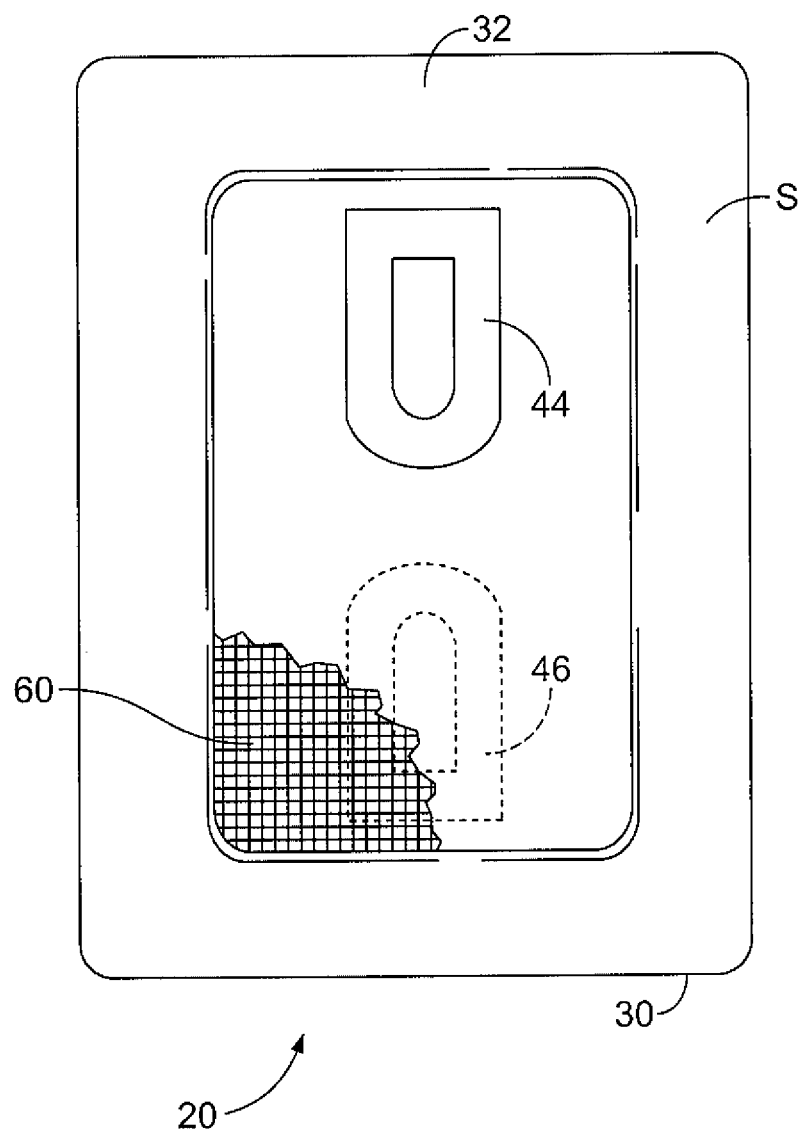
FIG. 1 is a plan view of one embodiment of a plasma filter according to the present disclosure.
Figure 2:
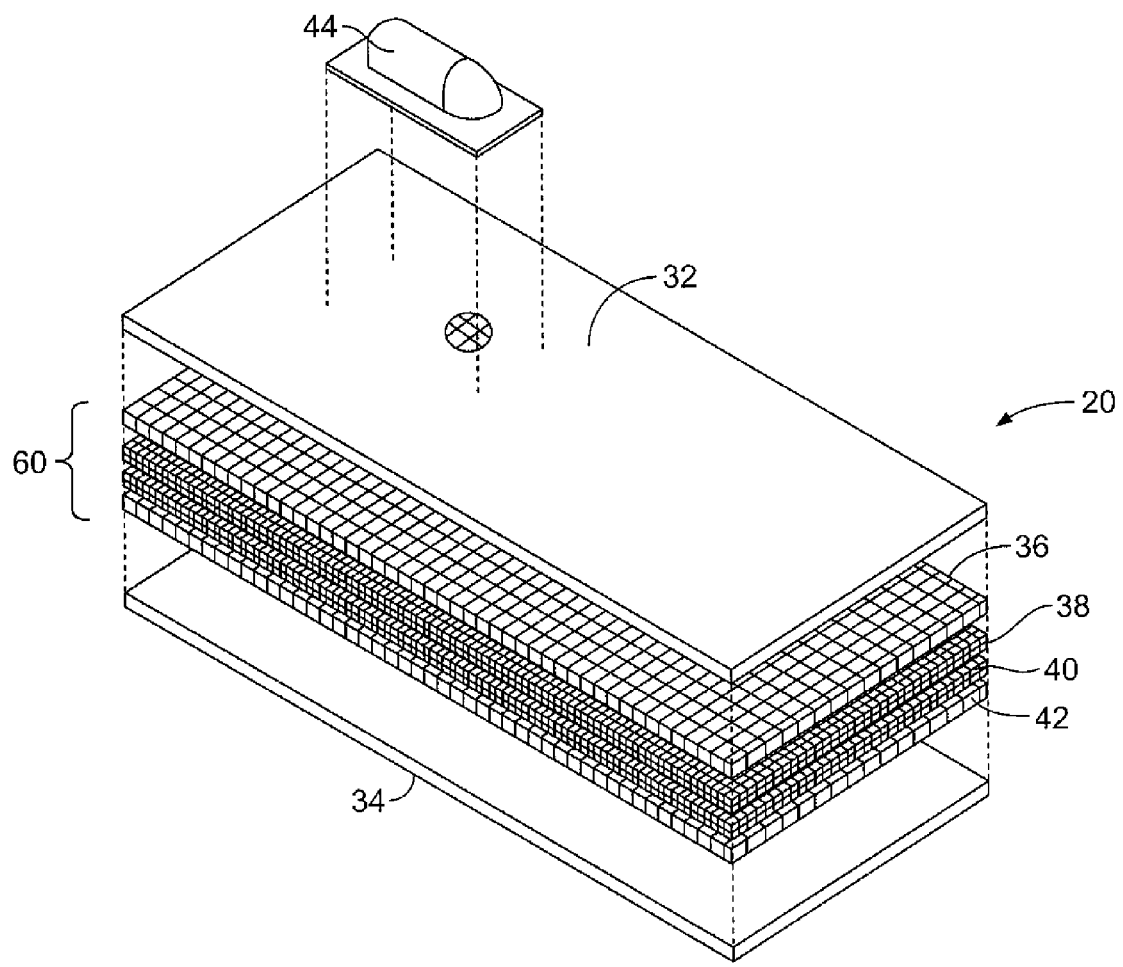
FIG. 2 is an exploded perspective view of the plasma filter of FIG. 1.

With reference to FIGS. 1 and 2, a filter 20 for use in a blood processing and storage system such as disclosed in the above-identified '905 patent is shown. Such a filter 20 is typically used for plasma filtration. For ease of understanding, only the plasma filter 20 is shown, although it should be understood that it forms part of a system that also typically may include one or more blood collection, processing and storage containers, donor tubing connected to a phlebotomy needle, a sampling device, transfer tubing interconnecting the various containers, auxiliary containers for various additives (such as red blood cell additive solution), and a leukocyte filter, as well as various combinations of one or more of the above, none of which is shown.

Typically, after whole blood has been collected from a donor into a blood processing container, the processing container, together with the integrally attached downstream containers and tubing, is placed into a conventional centrifuge. There, the whole blood is centrifugally separated into red blood cells and blood cell-depleted plasma. The cell-depleted plasma or "cell-poor" plasma is then expressed from the blood processing container into a plasma collection container, from which it may be passed through the filter 20 into a plasma storage container.

The filter 20 comprises a filter media, generally designated 60, that may be made up of three layers 36, 38 and 40 which are designed to remove by exclusion the red blood cells, platelets, and leukocytes typically found in plasma. The filter media 60 is enclosed within a housing 30 comprising first and second portions or sheets 32 and 34 of a preferably flexible, medical grade plastic material, such as polyvinyl chloride plasticized with di-2-ethylhexyl-phthalate (PVC-DEHP). A peripheral seal S of the various layers is formed using conventional sealing techniques, such as radio frequency heat sealing technology, to join the sheets 32 and 34 about the filter media.

Three layers 36, 38 and 40 make up the illustrated filter media 60 and are arranged serially in the flow path within the housing, one downstream of the other in the order of blood flow through the filter.

The first layer 36 comprises a prefilter that serves to remove fibrin clots and other large sized aggregates from the plasma, but may also retain cellular blood species by affinity, mostly the red cells. In practice, the prefilter layer 36 may comprise a borosilicate microfiber glass material with an acrylic binder resin, and will be described in greater detail below.

Second and third filter media layers 38 and 40 possess pore sizes which are approximately 10-fold smaller than the size of leukocytes, and which decrease in the direction of flow. Due to their pore size, the second and third filter media layers 38 and 40 remove red blood cells, platelets and leukocytes by exclusion. In practice, the second and third layers 38 and 40 may be of any suitable material and may comprise, solely or in combination with other materials, hydrophilic polyvinylidene fluoride (PVDF) membranes. The PVDF material of the second filter media layer 38 has an average pore size of about 1.0 microns, while the PVDF material of the third filter media layer 40 has a smaller average pore size of about 0.65 micron. The filter may also, if appropriate, employ only one of the second or third filter layers, or more than two such filter layers.

The downstream-most, in the direction of flow, last layer 42 comprises a mesh material preferably made from a polyester or polypropylene material. The mesh material of the last layer 42 provides mechanical support for the filter and prevents the PVDF material of the third filter layer from sticking, during use, to the portion or PVC sheet 34 around the outlet port 46 of the filter.

The plasma filter 20 includes inlet and outlet ports 44 and 46, and the filter media 60 is located in the flow path within the housing between the inlet and outlet. In use, the inlet port 44 conveys plasma into the housing and into contact with the prefilter layer 36. Plasma flows through the prefilter layer 36 and then through the second and third PVDF layers 38 and 40 where the removal of red blood cells and platelets, and leukocytes, occurs by exclusion. The outlet port 46 conveys plasma essentially free of blood cells through the mesh material.

In use, it has been found that the prefilter layer 36 is sometimes damaged such as by mishandling during, e.g., blood collection and centrifugation. For example, the prefilter may be damaged by handling impact or pressure from other portions of the fluid filter set or system during centrifugation. This can compromise the effectiveness of the filter 20, resulting in long filtration times due to clogging of the PVDF filter membranes.

Figure 3:
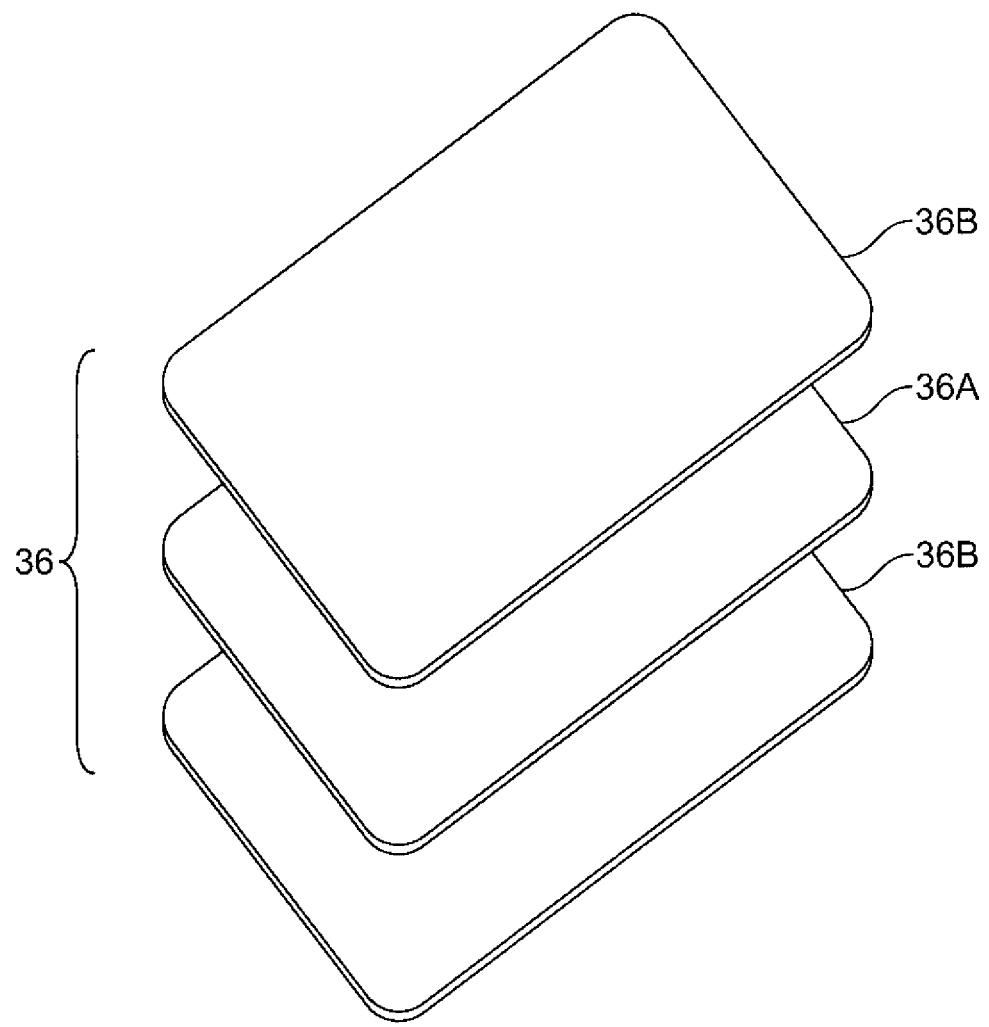
FIG. 3 is an exploded perspective view of a first embodiment of a prefilter membrane according to the present disclosure.

In keeping with the present disclosure, a plasma filter having a more robust prefilter membrane 36 is provided. With reference to FIG. 3, the prefilter layer 36 comprises a glass fiber membrane 36A that is carried by or adhered to (for example, laminated to) a reinforcing material 36B. The reinforcing material 36B is preferably a relatively high strength porous material, such as a textured, non-woven polyester fabric. The glass fiber membrane 36A is preferably laminated between two sheets of such reinforcing material 36B. One such laminated membrane 36 is available from Lydall Filtration/Separation Inc., of Manchester, Conn., as LyPore Grade 9390-A/A micro glass filtration material. In an alternative embodiment, the glass fiber membrane 36A may be carried by or adhered to (e.g., laminated to) only a single sheet of the reinforcing material 36B, preferably on the upstream side of the glass fiber membrane 36A.

The laminated prefilter 36 described in the preceding paragraph may be sized to have the same dimensions as the first and second filter layers 38, 40, as shown in FIG. 1. This results in the peripheries of the layers 36, 38, 40 all being sandwiched together between the sheets 32, 34 and all being heat sealed together by the application of, e.g., radiofrequency energy. If the reinforced prefilter is laminated to only a single layer of reinforcing material 36B, the filter is assembled with the reinforcing material 36B positioned on the upstream side of the glass fiber membrane 36A.

Figure 4:
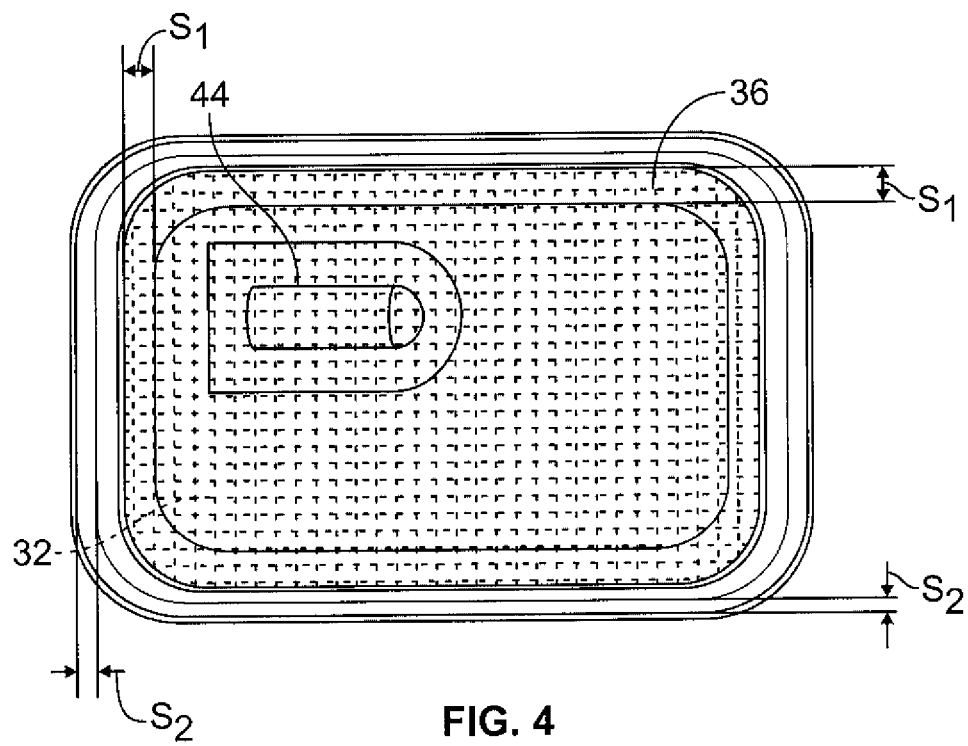
FIG. 4 is a plan view of the inlet side of an alternate embodiment of the plasma filter of FIGS. 1 and 2.
Figure 5:
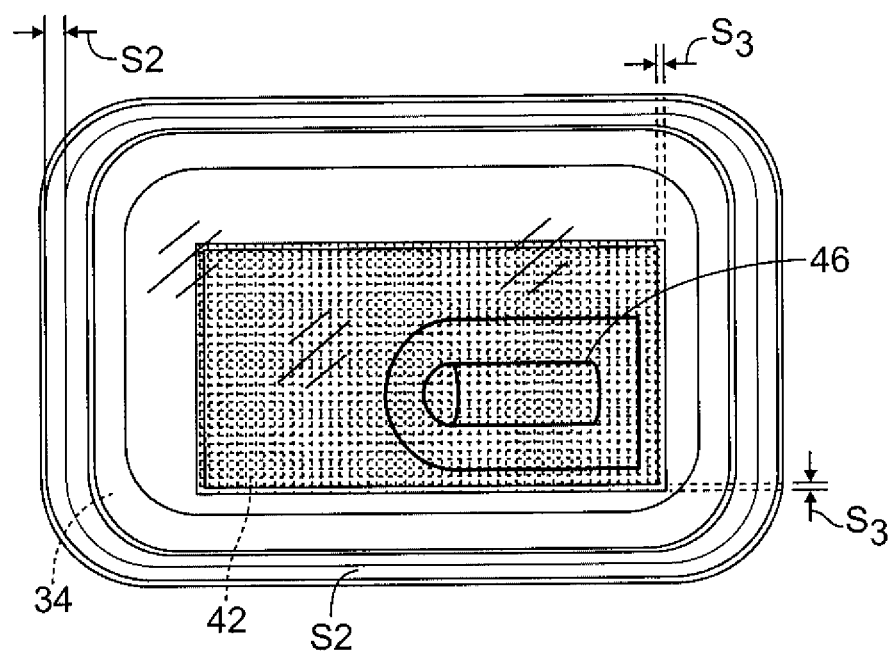
FIG. 5 is a plan view of the outlet side of a plasma filter according to the present disclosure.

In an alternative configuration, the laminated prefilter 36 and the first and second filter layers 38, 40 may be all sized at the same dimensions and all sealed only to one of the housing portions, such as the sheet 32 of the housing 30 at $S_1$ inboard of the conjoined edges $S_2$ of the sheets 32, 34 as shown in FIG. 4. It is believed that such a separate seal $S_1$ for the prefilter layer 36 and the filter layers 38, 40 to the housing layer 32 helps to ensure a better tightness of seal $S_2$ and to enhance the integrity of the prefilter. The glass fiber membrane 36A reinforced on the upstream side helps to minimize the forces to which the glass fiber membrane 36A is subjected during centrifugation and other handling of the processing and storage system, thus reducing the likelihood of damage during handling of the blood processing and storage system. Similarly, the fourth layer 42 may be smaller in size than the layers 38, 40 and be sealed independently of the other filter layers on a portion of the PVC sheet 34 surrounding the outlet port sealing area by a peripheral seal $S_3$, as best seen in FIG. 5.

Thus, the plasma filter may be preferably manufactured by first pre-cutting the three filter materials (pre-filter 36, first filter layer 38, and second filter layer 40) all to the same size and shape. Then the three filter materials may be pre-sealed at $S_1$ to the inlet housing sheet 32. After the mesh support layer is sealed at $S_3$ to the outlet housing sheet 34, the housing sheets 32 and 34 are sealed together at $S_2$.

Thus, an improved plasma filter has been disclosed, both alone and in combination with other fluid flow elements, such as tubing, clamps and other filters, that may be employed in a pre-assembled system for blood plasma collection and processing. The description provided above is intended for illustrative purposes only, and is not intended to limit the scope of the invention to any particular embodiment described herein. Instead, the scope is to be as set forth in the appended claims.

The invention claimed is:

1. A plasma filter for separating aggregates and targeted blood cell species from plasma, comprising:
   a filter housing including an inlet and outlet and an internal flow path between the inlet and outlet;
   filter media disposed in the flow path between the inlet and outlet for filtering plasma passing therethrough;
   the filter media comprising (a) a filter configured to substantially remove targeted blood cell types from the plasma and (b) a prefilter upstream of the filter;
   the prefilter including at least one reinforcement layer to which the prefilter is laminated.

2. The plasma filter of claim 1 wherein the prefilter includes a glass fiber layer.

3. The plasma filter of claim 2 wherein the reinforcement layer comprises a non-woven polyester material.

4. The plasma filter of claim 1 wherein the prefilter includes at least two reinforcing layers and a filter layer between the reinforcing layers.

5. The plasma filter of claim 1 wherein the housing comprises first and second plastic housing portions being sealed together along facing peripheral surfaces, the filter includes a peripheral edge portion located between the facing peripheral surfaces of the first and second plastic housing portions.

6. The plasma filter of claim 5 wherein no portion of the prefilter and filter membranes are located between the facing peripheral surfaces of the first and second plastic housing portions.

7. The plasma filter of claim 1 wherein the filter housing is flexible.

8. The plasma filter of claim 1 wherein the filter media comprises a membrane having pores sized to remove targeted blood cell types.

9. The plasma filter of claim 1 wherein the filter media comprises a plurality of porous membranes.

10. The plasma filter of claim 1 wherein the housing comprises first and second housing portions and the prefilter and filter membranes are sealed to only one of the first and second housing portions.

11. A plasma filter for separating aggregates and targeted blood species from plasma comprising:
   a first housing layer;
   a prefilter for removing the aggregates from the plasma;
   first and second filter membranes having pores sized to remove targeted cellular blood species from plasma by exclusion;
   a mesh layer; and
   a second housing layer;
   wherein the prefilter is laminated to at least one reinforcement layer.

12. The plasma filter of claim 11 wherein the reinforcement layer for the prefilter comprises a non-woven polyester fabric.

13. The plasma filter of claim 11 wherein the prefilter is laminated between two reinforcement layers.

14. The plasma filter of claim 11 wherein the reinforced prefilter and filter membranes are sealed only to the first housing layer.

15. The plasma filter of claim 4, wherein the filter layer has a first face in contact with one of the at least two reinforcing layers and a second face in contact with the other of the at least two reinforcing layers.

16. The plasma filter of claim 1, wherein the housing comprises first and second housing portions sealed together along peripheral surfaces and wherein the filter comprises a filter peripheral edge portion sealed to the first housing portion inboard of the peripheral surfaces of the first and second housing portions.

17. The plasma filter of claim 16 further comprising a mesh layer having a mesh peripheral edge portion sealed to the second housing portion inboard of the filter peripheral edge portion.

18. The plasma filter of claim 11, wherein the first and second housing layers are sealed together along peripheral surfaces and wherein the prefilter comprises a prefilter peripheral edge portion sealed to the first housing layer inboard of the peripheral surfaces of the first and second housing layers.

19. The plasma filter of claim 18, wherein the mesh layer has a mesh peripheral edge portion sealed to the second housing portion inboard of the prefilter peripheral edge portion.

20. A plasma filter for separating aggregates and targeted blood species from plasma, the plasma filter comprising:
   a first housing layer;
   first and second filter membranes having pores sized to remove targeted cellular blood species from plasma by exclusion;
   a mesh layer;
   a second housing layer;
   a prefilter for removing the aggregates from the plasma;
   a first reinforcement layer laminated against a first face of the prefilter; and
   a second reinforcement layer laminated against a second face of the prefilter.

* * * * *